US005792744A

United States Patent [19]
Ronchi et al.

[11] Patent Number: 5,792,744
[45] Date of Patent: Aug. 11, 1998

[54] PROTEINS FROM MAMMALIAN LIVER

[75] Inventors: Severino Ronchi; Alberto Bartorelli, both of Milan, Italy

[73] Assignee: Zetesis S.p.A., Milan, Italy

[21] Appl. No.: 765,957

[22] PCT Filed: Jul. 12, 1995

[86] PCT No.: PCT/EP95/02723

§ 371 Date: Feb. 6, 1997

§ 102(e) Date: Feb. 6, 1997

[87] PCT Pub. No.: WO96/02567

PCT Pub. Date: Feb. 1, 1996

[30] Foreign Application Priority Data

Jul. 14, 1994 [IT] Italy ............... MI94A001469

[51] Int. Cl.$^6$ ............... A61K 38/00; C07K 14/00
[52] U.S. Cl. ............... 514/2; 514/12; 530/300; 530/412
[58] Field of Search ............... 530/300, 412; 514/2, 12

[56] References Cited

FOREIGN PATENT DOCUMENTS 0 574 394  5/1995  European Pat. Off.
92 10197  6/1992  WIPO.

OTHER PUBLICATIONS

Reeck et al (Cell, 1987, 50:667).
Lewin (Science, 1988, 237:1570).
Eur. J. Biochem. (1993), 212(3), 665–73, "Characterization, purification and cDNA cloning of a rat perchloric–acid–soluble 23–kDa protein present only in liver and kidney", Levy–Favatier et al.
Database EMBL, Emrod:Respspl; Access–no: D49363, "Sequence of PSP1", T. Oka, 22. Feb. 1995, See Abstract.
Database EMBL, Emest:Hs68065, Access–no: T98680, "The WashU–merck EST Project", L. Hillier et al, 17 Apr. 1995, See Abstract.

Primary Examiner—Lila Feisee
Assistant Examiner—Susan Ungar
Attorney, Agent, or Firm—Griffin, Butler Whisenhunt & Szipl, LLP

[57] ABSTRACT

The present invention relates to proteins that may be extracted from mammalian livers. The proteins of the invention have a molecular weight of 14 Kda as measured by SDS-PAGE electrophoresis and comprise the sequence identified in the application as Sequence No. 1. The proteins of the invention may be incorporated in pharmaceutical agents, used as diagnostic tools in oncology and used in the treatment of neoplastic diseases.

7 Claims, No Drawings

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( v ) FRAGMENT TYPE: internal ( v i ) ORIGINAL SOURCE:
        ( A ) ORGANISM: Capra hircus
        ( F ) TISSUE TYPE: Liver ( x i ) SEQUENCE DESCRIPTION: SEQ ID NO: 1:

```
Met Asp Pro Ala Ser Gly Gln Leu Val Pro Gly Gly Val Val
 1               5                  10
Glu Glu Ala Lys Gln Ala Leu Thr Asn Ile Gly Glu Ile Leu
15                  20                  25
Lys Ala Ala Gly Xaa Asp Phe Thr Asn Val Val Lys Ala Thr
    30                  35                  40
Val Leu Leu Ala Asp Ile Asn Asp Phe Xaa Ala
        45                  50
```

PROTEINS FROM MAMMALIAN LIVER

The present invention refers to proteins from animal tissues, particularly from mammalian liver, and to the use thereof in oncology.

WO 92/10197 discloses extracts of mammalian organs, particularly of goat liver, consisting of at least three different proteins and characterized by unusual pharmacological and immunological properties. No information was reported on the actual role and on the sequences of the individual protein components.

A 23-KDa dimeric protein extracted with 5% perchloric acid from rat liver and kidney has been disclosed in Eur. J. Biochem. 212, 665, 1993. The corresponding cDNA sequence have been deposited at the EMBL data bank under accession number X70825.

This protein, reported to be co-extracted with High-mobility group (HMG) proteins, is suggested to play a role in the folding of proteins, so that it could be considered as one member of the class of the so-called "chaperons" or chaperonins.

WO 93/18146 discloses a protein extracted from rabbit-liver having a molecular weight of 59 Kd capable of complexing with chaperons and a heat shock protein of 90 Kd.

A new protein purified from the extract disclosed in WO 92/10197, has been found now having the partial aminoacid sequence depicted in sequence Id No. 1.

Said protein is useful in oncology in view of the following properties:

the serum of animals immunized with the protein displays cytotoxic activity against human tumor cell cultures;

the protein has marked antineoplastic activity at the dose of 0.015 µg/kg in Balb/c mice having a murine colon adenocarcinoma (c26) and in rats with intrapleuric Yoshida ascitic tumor;

when administered to animals, man included, it raises antibodies able to recognize human carcinoma cells.

Said properties explain the activity observed in clinical tests carried out administering the extract of WO 92/10197 to patients affected by advanced cancer of the lung, breast, stomach, colon and liver.

The protein of the invention has a high degree of homology with that extracted from rat liver disclosed in Eur. J. Biochem. 212, 665, 1993.

Proteins having a high degree of homology with that of Sequence Id No. 1 have also been found in liver of different animal species, particularly bovine and equine liver.

A new protein family has been therefore found: the members of this previously unknown family are characterized by an high degree of conservation and homology between the mammalian species and a molecular weight ranging from about 10 KDa to about 14 KDa.

The term "high degree of homology" means an homology of the aminoacid sequences of about 80% or higher, preferably of 90% or higher.

The invention further refers to the use in oncology, as a therapeutic and/or diagnostic tool, of the above mentioned perchloric acid extractable proteins from mammalian liver.

The invention provides therefore pharmaceutical compositions containing the protein having the partial amino acid sequence No. 1 or proteins having at least 80% homology, preferably at least 90% homology, with Sequence Id No. 1.

The pharmaceutical compositions of the invention will be administered by parenteral route, preferably subcutaneously or intra-muscularly and will typically contain from 0.1 to 50 mg of total protein per unit dose. The protein active principle, purified by conventional methods, may be lyophilized on a suitable non-toxic carrier and distributed in vials or bottles.

Suitable solvents include sterile water or saline solutions.

According to a further embodiment of the invention, the proteins of the invention or fragments thereof, produced for instance by chemical synthesis, may be used to produce polyclonal or monoclonal antibodies. Particularly interesting antibodies recognize tumoral antigens and are therefore useful for diagnostic, therapeutic or research purposes. Two of said antibodies have been deposited on 27 Jul., 1993 at the European collection of Animal Cell Cultures (EGACC), Porton Down, Salisbury, UK under accession numbers 930806103 and 930806104.

These antibodies were used in immunocytochemical tests on several bioptic samples of human cancers, enabling their recognition.

The proteins of the invention, when administered to patients affected by neoplastic disease, in addition to advantageous effects such as inhibition or regression of the tumoral mass, reduction of pain and improvement of cenestesis, raise antibodies having marked cytotoxic action on cultured tumor cells. The whole serum, not free from the complement cascade, is required for said cytotoxic effect.

When used for therapeutic purposes or as a vaccine to induce immunity against neoplastic transformation, the proteins of the invention may be administered at a dosage ranging from 0.1 to 30 mg/day/patient, by the subcutaneous, intramuscular or intravenous route. The treatment will be repeated even for long periods, until the concentration of the raised antibodies reaches a convenient level.

The concentration of the raised antibodies may be determined by conventional methods, using for instance immunoenzymatic techniques. To this purpose, the invention provides diagnostic kits containing suitably labelled reagents, e.g. the protein of the invention or fragments thereof as an antigen, optionally immobilized on a suitable support, anti-Ig antibodies and suitable reagents able to detect, e.g. by means of a colorimetric reaction, an antigen-antibody complex.

The proteins of the invention may advantageously be administered together with suitable carriers, acting as adjuvants. Suitable adjuvants may be selected, for instance, from non-toxic proteins, preferably xenogenic proteins, e.g. proteins from the same species from which the immunogenic protein is extracted.

The proteins of the invention are prepared by subjecting the crude extract, obtained by extracting the organs with perchloric acid and subsequently with hypertonic saline solutions (KCl 3M for instance) and subsequent dialysis, to purification steps in HPLC and hydrophobic exchange chromatography (FPLC) as hereinafter specified in the Examples.

The protein obtained from goat liver is blocked at the N-terminal and it has been therefore partially sequenced after cleavage with CNBr, yielding two main fragments having molecular weight (determined by the MALDI-TOF method) respectively of 10263 and 4063 D, respectively, whereas the molecular weight before cleavage is 14.290 Daltons, in agreement with the value determined by SDS-PAGE electrophoresis.

The following examples further illustrate the invention.

EXAMPLE 1

A liver goat extract, prepared as in WO 92/10197, and hereinafter referred to as UK 101, is concentrated on Amicon PM 10 membrane and subsequently dialyzed against $NaH_2PO_4/Na_2HPO_4$, 0.01M, pH 6.5. The product is purified by HPLC on TSK DEAE 5 PW equilibrated in said buffer; the starting buffer is collected and the protein absorbed on the resin are eluted with 1M NaCl. The peak eluted in the starting buffer is subsequently purified by HPLC on TSK SW 3000 column.

Two main peaks are obtained by this chromatography: the first is discarded since it mainly consists of glycogen; the second, particularly rich in low molecular weight proteins, is then purified by FPLC on Protein-Pac HIC Phenyl 5 PW column.

The purification on this hydrophobic exchange column, is carried out in the following conditions: a starting buffer, Tris HCl 20 mM pH 7 containing $(NH_4)_2SO_4$ 1M, is first eluted, followed by a linear gradient elution ending with Tris- HCl 20 mM without ammonium sulfate. The starting buffer is discarded whereas the zone, eluted in the gradient at a $(NH_4)_2SO_4$ molarity ranging from 0.6 to 0.8M is collected and dialyzed against $H_2O$.

A sample hereinafter referred to as UK 114 showing a protein band in SDS-PAGE of about 14 Kda with a purity degree of about 90% is obtained.

EXAMPLE 2

In immunocytochemical tests, polyclonal antibodies raised in rabbits immunized with liver goat extract (WO 92/10197) administered subcutaneously in PBS with Freund's complete adjuvant every week for 2 months were used.

Monoclonal antibodies were obtained from Balb/c mice one month after weekly subcutaneous injections of 100 µg of UK 101 with incomplete Freund's adjuvant. The fusion with myeloma cells of lymphocytes obtained from animals immunized against UK 101 was carried out by conventional methods. Two of the obtained hybridomas were deposited on 27 Jul., 1993 at the European Collection of Animal Cell Cultures (ECACC) Porton Down, Salisbury, UK, under accession numbers 930806103 and 930806104.

The antibodies secreted by said hybridome recognize the proteins of the invention.

The mono- and polyclonal antibodies have been assayed in immunocytochemistry tests on 30 bioptic samples of malignant tumors isolated from different organs such as breast, lung, bladder, stomach, colon-rectum, uterus, soft tissues, prostate. The tissues were fixed in 10%, buffered formaline and preparations in paraffine were stained by means of Mistostain Kit SP, Zymed Lab. Inc.

The sections were incubated with the antibodies (0.5 µg/ml of Ig with 1% BSA/PBS) overnight at 4° C. After washing, the slides were incubated with anti-rabbit pig biotinylated Ig for 60 minutes and then for other 60 minutes with a 1:100 dilution of peroxidated streptavidine-biotine complex. The peroxidase binding was detected using the 3,3-diaminobenzidine/$H_2O_2$ reaction. Only the tissue showing specific reaction against the antibodies in the cytoplasma were considered positive. The immunoreactivity was considered as negative, slightly positive, positive (++) and highly positive (+++) for the normal tissues. The results are reported in the following Table. The immunocytochemical reactivity with different polyclonal antibodies anti goat, calf and horse liver extract is detectable in most malignant tumors (82.7% for antibodies against horse liver extract and 100% for calf liver extract). The monoclonal antibody secreted by the hybridoma No. 930806103 gave positive results for 93.7% of the assayed tumors.

TABLE

Immunocytochemical reactivity of malignant tumors (+/−)

| SITE | Anti UK101 | | | Mab n. |
| --- | --- | --- | --- | --- |
| | Goat | Calf | Horse | 930806103 |
| Breast | 4/0 | 1/0 | 1/0 | 1/0 |
| Stomach | 4/3 | 3/0 | 3/0 | 3/0 |
| Colon/rectum | 7/0 | 5/0 | 5/0 | 5/0 |
| Lung | 1/1 | n.a. | n.a. | 1/0 |
| Bladder | 2/0 | 1/0 | 1/0 | 1/0 |
| Prostate | 3/0 | 1/0 | 1/0 | 1/1 |
| Uterus | 1/0 | 1/0 | 1/0 | 1/0 |
| Adrenal gland | 1/0 | 1/0 | 1/0 | 1/0 |
| NOS | 2/1 | 1/0 | 0/1 | 1/0 |
| Total | 25/5 | 14/0 | 13/1 | 15/1 |

WO 96/02567   PCT/EP95/02723

INTERNATIONAL FORM

TO
Zetesis spa
Galleria del Corso
2 Milano
Italy

NAME AND ADDRESS OF DEPOSITOR

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: | Accession number given by the INTERNATIONAL DEPOSITARY AUTHORITY: |
| P3D1D11 | 930806103 |

| II. SCIENTIFIC DESCRIPTION AND/OR PROPOSED TAXONOMIC DESIGNATION |
|---|
| The microorganism identified under I above was accompanied by: |
| [X] a scientific description |
| [ ] a proposed taxonomic designation |
| (Mark with a cross where applicable) |

| III. RECEIPT AND ACCEPTANCE |
|---|
| This International Depositary Authority accepts the microorganism identified under I above, which was received by it on 06.08.93 (date of the original deposit)[1] |

| IV. RECEIPT OF REQUEST FOR CONVERSION |
|---|
| The microorganism identified under I above was received by this International Depositary Authority on (date of the original deposit) and a request to convert the original deposit to a deposit under the Budapest Treaty was received by it on (date of receipt of request for conversion) |

| V. INTERNATIONAL DEPOSITARY AUTHORITY | |
|---|---|
| Name: Dr A Doyle | Signature(s) of person(s) having the power to represent the International Depositary Authority or of authorized official(s): |
| Address: ECACC CAMR | Date: 8 March 1994 |

[1] Where Rule 6.4(d) applies, such date is the date on which the status of international depositary authority was acquired.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
Zetesis spa
Galleria del Corso
2 Milano
Italy

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name: Zetesis spa<br><br>Address: Galleria del Corso<br>2 Milano<br>Italy | Accession number given by the<br>INTERNATIONAL DEPOSITARY AUTHORITY:<br><br>930806103<br><br>Date of the deposit or of the transfer:<br><br>6 August 1993 |

III. VIABILITY STATEMENT

The viability of the microorganism identified under II above was tested on 6 August 1993 [1][2]. On that date, the said microorganism was

[X] viable [3]

[ ] no longer viable [3]

---

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

We claim:

1. A purified protein comprising the amino acid sequence of Sequence ID No. 1 and having a molecular weight of about 14 Kda determined by SDS-PAGE electrophoresis.

2. A protein according to claim 1, extracted from goat, horse, or calf liver.

3. A protein according to claim 2, extracted from goat liver.

4. Compositions comprising a unit dosage of from 0.1 to 50 mg of a protein of claim 1 in admixture with a pharmaceutically acceptable carrier.

5. A protein according to claim 1, being about 90% purified.

6. A protein according to claim 1, extracted from horse liver.

7. A protein according to claim 1, extracted from calf liver.

* * * * *